US005632954A

United States Patent [19]

Coellner et al.

[11] Patent Number: 5,632,954

[45] Date of Patent: May 27, 1997

[54] METHOD FOR KILLING MICROORGANISMS

[75] Inventors: James A. Coellner; Henry Mark, both of Philadelphia, Pa.

[73] Assignee: Engelhard/ICC, Philadelphia, Pa.

[21] Appl. No.: 647,278

[22] Filed: May 13, 1996

Related U.S. Application Data

[63] Continuation of Ser. No. 261,787, Jun. 20, 1994, abandoned.

[51] Int. Cl.$^6$ ....... A61L 9/00; B01D 19/00

[52] U.S. Cl. ....... 422/4; 422/5; 422/30; 55/279; 62/94; 62/271; 165/8

[58] Field of Search ....... 422/5, 4, 30; 55/279; 62/94, 271; 165/8

[56] References Cited

U.S. PATENT DOCUMENTS

| | | | |
|---|---|---|---|
| 1,215,222 | 2/1917 | Van Calcar et al. | 62/271 |
| 2,478,617 | 8/1949 | Anderegg | 62/140 |
| 2,765,046 | 10/1956 | Rondholz | 183/4 |
| 2,926,502 | 3/1960 | Munters et al. | 62/94 |
| 3,844,737 | 10/1974 | Macriss et al. | 55/34 |
| 4,228,847 | 10/1980 | Lindahl | 165/10 |
| 4,370,301 | 1/1983 | Doi et al. | 422/122 |
| 4,594,860 | 6/1986 | Coellner et al. | 62/271 |
| 4,786,301 | 11/1988 | Rhodes | 62/271 |
| 4,853,202 | 8/1989 | Kuznicki | 423/326 |
| 4,905,479 | 3/1990 | Wilkinson | 62/271 |
| 4,955,205 | 9/1990 | Wilkinson | 62/94 |
| 5,148,374 | 9/1992 | Coellner | 364/505 |
| 5,170,633 | 12/1992 | Kaplan | 62/94 |
| 5,176,005 | 1/1993 | Kaplan | 62/94 |
| 5,327,739 | 7/1994 | Ingersoll et al. | 62/78 |
| 5,353,606 | 10/1994 | Yoho et al. | 62/271 |

OTHER PUBLICATIONS

R.E. Chant, "Microbiological Testing of a Cargocaire/Munters Honeycombe Desiccant Dehumidifier. Phase 1: Static Tests and Phase II: Dynamic Tests", The University of Manitoba, Department of Mechanical Engineering, Winnipeg, Manitoba, Canada, Phase 1: [(Feb., 1986) pp. (i)–17; (Sep., 1986) Phase II: pp. (i)–21].

"Kathabar®. . . provides precision humidity control under all conditions", (Product Brochure for Kathabar Systems Division, New Brunswick, NJ, (12 pages).

"Research Bulletin: The Antibacterial Effects of Glycol Compounds used in No Frost® Refrigeration and Hygol® Dehumidifications Systems", (Product Brochure for Niagara Blower Company, Buffalo, N.Y., Nov. 14, 1988, (4 pages).

*Primary Examiner*—Nina Bhat

*Attorney, Agent, or Firm*—Panitch Schwarze Jacobs & Nadel, P.C.

[57] ABSTRACT

The concentration of airborne microorganisms can be substantially reduced by passing air containing a concentration of microorganisms through a core of desiccant. Preferably, the core of desiccant is present in a moisture transfer wheel, which forms part of an open-cycle air conditioning system. The preferred desiccant is a large-pored crystalline titaniumsilicate molecular sieve, which can be regenerated into an essentially anhydrous state at a regeneration temperature of less than about 200° F., and thereafter can absorb moisture from air to provide air having a vapor pressure of less than about 3 torr.

18 Claims, 2 Drawing Sheets

METHOD FOR KILLING MICROORGANISMS

CROSS-REFERENCE TO RELATED APPLICATION

This is a continuation of U.S. patent application No. 08/261,787, filed Jun. 20, 1994, now abandoned.

FIELD OF THE INVENTION

The present invention relates to a method for killing microorganisms and, more particularly, to a method of operating a desiccant air conditioner so as to treat microorganism-laden air in a manner which substantially reduces the concentration of microorganisms in the treated air.

BACKGROUND OF THE INVENTION

There is a growing public awareness of, and concern for, the health effects attendant contact with air-borne microorganisms. The concern is particularly acute as regards the air quality in enclosed spaces, such as home and workplace. Workplaces including breweries; pharmaceutical manufacturing, formulation and encapsulation sites; hospital critical areas such as surgery and intensive care units; and semiconductor manufacturing sites are all very susceptible to disruption by the presence of various airborne microorganisms.

As many homes and workplaces are already equipped with air conditioning systems, it would be convenient if means were available for operating an air-conditioner in a manner lethal to airborne microorganisms.

Open-cycle air-conditioners are known in the art and are based primarily on the Munters Environmental Control system (MEC) unit as described in U.S. Pat. No. 2,926,502. As set forth in this patent, the basic open-cycle air-conditioner operates by dehumidification and subsequent cooling of air wherein moist hot air is conditioned by basically a multistage process to produce cool air.

In open-cycle air-conditioning systems, a basic multistep approach is used. In the inlet path, outside air is subjected to removal of moisture through a moisture transfer wheel, with the dried air being cooled by means of a heat exchanger wheel with the subsequent addition of moisture by an evaporative element so as to further cool the air before it enters the area to be conditioned. In the return cycle, the air passes through an exhaust path which includes a further evaporative element, the heat exchanger wheel, a heating element, and the moisture transfer wheel, after which the air is exhausted to the atmosphere. In the return cycle, also called the outlet path, air passing through the moisture transfer wheel accomplishes the regeneration of the wheel by driving moisture therefrom.

One of the major advantages of this type of system is that a constant supply of fresh, filtered air is delivered to the space to be conditioned as opposed to the recirculation of air as is found in standard heating and cooling systems.

The basic principle of the MEC system is that dry warm air can be simultaneously cooled and humidified by contacting it with water vapor. However, in geographic areas where the air is both warm and humid, it must be dried before it can be cooled by evaporation. The efficiency and the effectiveness of an open-cycle air-conditioning system depends upon the ability of the unit to dehumidify the warm moist air input, and upon the effectiveness of the heat exchanger wheel or unit.

As to the heat exchanger wheel, operation depends upon the opposite faces remaining at different temperatures. This means that there must be a significant temperature gradient across the wheel in the axial direction. Proposed use of highly thermally conductive material such as metal results in the temperature gradient through the wheel being substantially less, with poor heat exchange and low effectiveness. In the open-cycle air-conditioner system, the heat created by the drying of the air by the moisture transfer wheel must be removed by the heat exchanger wheel. However, migration of the heat axially in the direction of flow of the air through the wheel must be kept to a minimum. If the heat does not migrate, the air stream to be treated exiting from the heat exchanger wheel will not be sufficiently cooled to render the system practical for air-conditioning reasons because the evaporator would not be capable of reducing the higher temperature to an acceptable level of temperature and humidity.

There is a need in the art for an effective air conditioning system that treats air so as to accomplish a substantial reduction in the concentration of air-borne microorganisms, where the treatment is accomplished without exposing the air to toxic chemicals. The present invention solves this need by providing a desiccant air conditioning system which employs a zeotite desiccant. Use of the present invention results in a safe and highly effective method for substantially reducing air-borne microorganisms, while at the same time providing temperature control and dehumidification of air.

SUMMARY OF THE INVENTION

Briefly stated, the present invention is directed a method for substantially reducing a concentration of microorganisms in air comprising passing air having the concentration of microorganisms through a desiccant air conditioning system having an inlet path, an outlet path and a moisture transfer wheel comprising zeolite. The moisture transfer wheel is positioned in the inlet and outlet paths and is movable such that the desiccant zones move between the inlet and outlet paths to degenerate and regenerate the zeolite.

Another aspect of the invention is a method for substantially reducing a concentration of microorganisms in air comprising passing air having the concentration of microorganisms through an open-cycle air-conditioning system. The system includes a rotatable heat exchanger wheel, a rotatable desiccant carrying moisture transfer wheel, a heater disposed between the heat exchanger wheel and moisture transfer wheel, an evaporator positioned on a side of the heat exchanger wheel opposite from the heater, and means for passing air through the heat exchanger wheel and the moisture transfer wheel in generally separate inlet and outlet paths.

A further aspect of the invention is a method for substantially reducing a concentration of microorganisms in air comprising passing the air having the concentration of microorganisms through an open-cycle air-conditioning system. The system includes a rotatable heat exchanger wheel, a rotatable zeolite carrying moisture transfer wheel, a heater disposed between the heat exchanger wheel and moisture transfer wheel, an evaporator positioned on a side of the heat exchanger wheel opposite from the heater, and means for passing air through the heat exchanger wheel and the moisture transfer wheel in an inlet path and an outlet path.

Another aspect of the invention is a method of controlling an open-cycle desiccant air conditioning system having a rotatable heat exchanger wheel, a rotatable desiccant carrying moisture transfer wheel, a heater disposed between the heat exchanger wheel and moisture transfer wheel, an evaporator positioned on a side of the heat exchanger wheel opposite from the heater, and means for passing air through the heat exchanger wheel and the moisture transfer wheel in an inlet path and an outlet path, to substantially reduce a concentration of microorganisms in air forced through the air conditioning system, comprising the steps of:

(a) inleting air to the system where the air has a temperature within the range of about 0° F. to about 120° F., and a vapor pressure of about 1 torr to about 25 torr;

(b) exiting inlet air from the moisture transfer wheel where the air has a vapor pressure of no more than 5 torr; and (c) drawing outlet air having a temperature not exceeding 200° F. through the moisture transfer wheel.

According to a preferred embodiment, the desiccant according to the invention is a zeolite. The zeolite is a crystalline titaniumsilicate molecular sieve zeolite having a pore size of approximately 8 Angstrom units and a composition in term of mole ratios of oxides as follows:

$1.0\pm0.25\ M_{2/n}O: TiO_2: y\ SiO_2: z\ H_2O$ wherein M is at least one cation having a valence of n, y is from 2.5 to 25, and z is from 0 to 100, the zeolite being characterized by an X-ray powder diffraction pattern having the lines and relative intensities as set forth in Table 1 below:

TABLE 1

XRD POWDER PATTERN OF ETS-10
(0–40° 2 theta)

| SIGNIFICANT d-SPACING (ANGS.) | $I/I_o$ |
|---|---|
| 14.7 = .35 | W–M |
| 7.20 = .15 | W–M |
| 4.41 = .10 | W–M |
| 3.60 = .05 | VS |
| 3.28 = .05 | W–M |

where VS = 60–100; S = 40–60; M = 20–40; and W = 5–20.

BRIEF DESCRIPTION OF THE DRAWINGS

The foregoing summary, as well as the following detailed description of the preferred embodiment of the invention, will be better understood when read in conjunction with the appended drawings. For the purpose of illustrating the invention, there is shown in the drawing an embodiment which is presently preferred. It should be understood, however, that the invention is not limited to the precise arrangements and instrumentalities shown. In the drawings.

DETAILED DESCRIPTION OF THE PREFERRED EMBODIMENTS

Certain terminology is used in the following description for convenience only and is not limiting.

Figure 1:
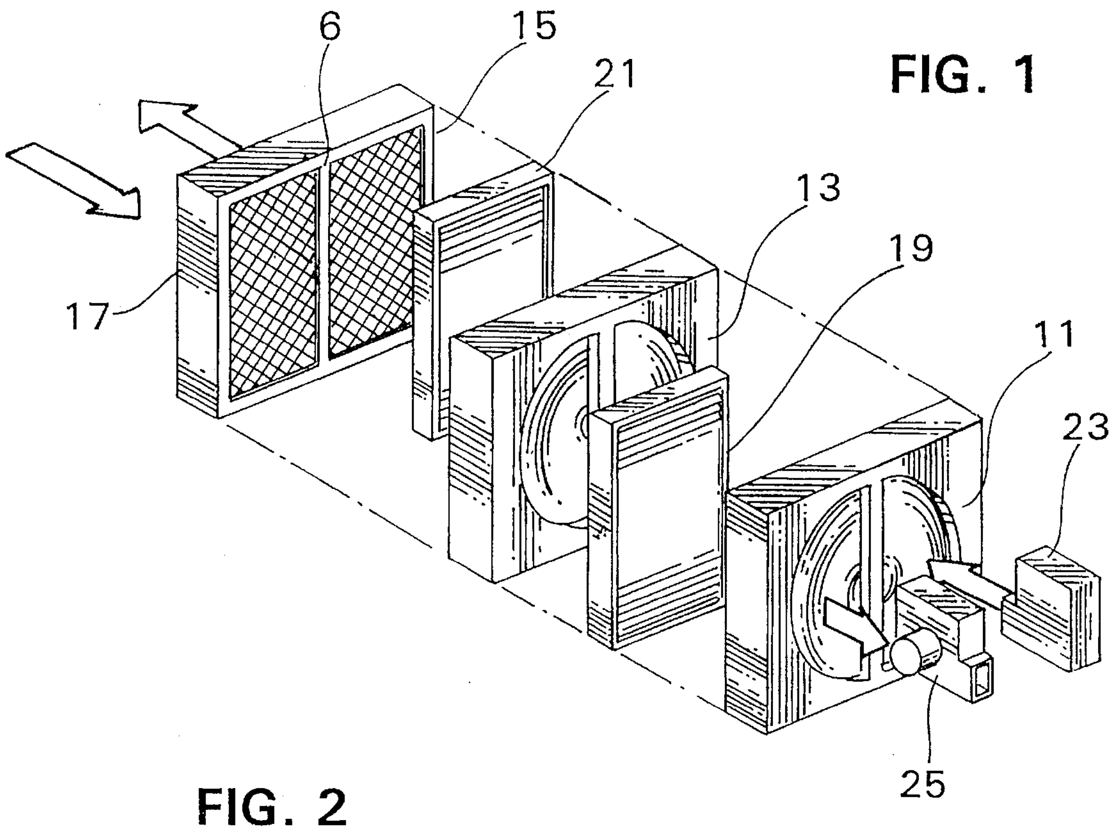
FIG. 1 is a diagrammatic perspective view of an open-cycle air conditioning system in accordance with the present invention.

Turning now to the drawings, FIG. 1 illustrates a schematic of the basic open-cycle air-conditioning system of the present invention. A moisture transfer wheel assembly 11 constitutes the exterior or outside element of the system. As will be noted and discussed later, the assembly 11 is separated into two sections so as to provide an intake path and an exhaust path through the assembly 11, as indicated by the arrows. A heat exchanger wheel assembly 13, also partitioned so as to provide intake and exhaust paths is located substantially adjacent to the moisture transfer wheel assembly 11, separated only by a solar heat regeneration coil 19. Auxiliary solar heating coil 21 may be placed in the system for use in cold months when it is desirable to heat the interior of the area rather than to cool it. The solar coils include fluid pipes which are interconnected with standard solar heating units (not shown). The basic unit terminates in a pair of evaporator elements 15 and 17 separated by a partition 6 with the arrows indicating the intake air into the building and the air exhausting therefrom. A supply blower 23 and a exhaust blower 25 are provided so as to implement the necessary air movement within the system. This particular open-cycle air conditioner system is disclosed in U.S. Pat. No. 4,594,860, the entire disclosure of which is hereby incorporated herein by reference. Accordingly, further description of the structure of the open-cycle air conditioner system is omitted for purposes of brevity only and is not limiting.

As is well known, this type of system provides removal of the moisture from the intake air by the moisture transfer wheel assembly 11. When moisture is removed from the air, the temperature of the air increases. The air is subsequently cooled upon passing through heat exchanger wheel assembly 13, which lowers the temperature of the warm dry air. Evaporator element 15 adds moisture to the air, thus reducing the temperature further and supplying cool air to the conditioned area. The exhaust air passes through evaporator element 17 and through heat exchanger wheel assembly 13 so as to remove heat from the heat exchanger and raise the temperature of the exhaust air. The temperature of the exhaust air is further raised by means of the solar heating element 19 so as to provide high temperature air in the exhaust path resulting in regeneration of the moisture transfer wheel assembly 11. The air from the moisture transfer wheel assembly 11 is exhausted into the atmosphere.

The two elements of the system which primarily govern the coefficient performance (COP) of the system are the moisture transfer wheel assembly 11 and the heat exchanger wheel assembly 13. With the exception of the specific material used in these wheels, they may be constructed in substantially the same manner.

Figure 2:
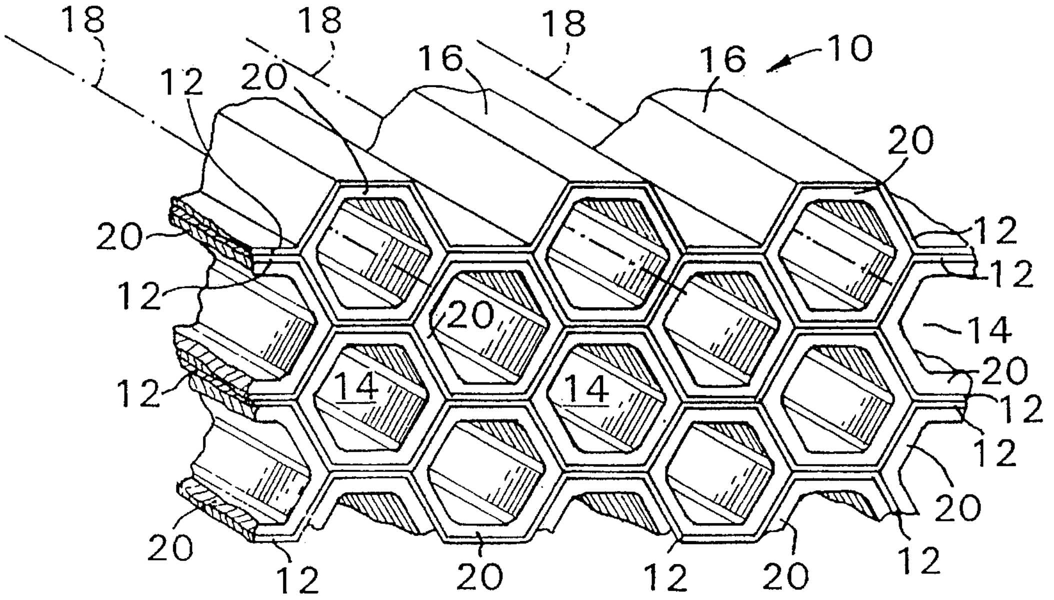
FIG. 2 is a greatly enlarged cross-sectional view of a core of a moisture transfer wheel used in the air conditioning system shown in FIG. 1.
Figure 3:
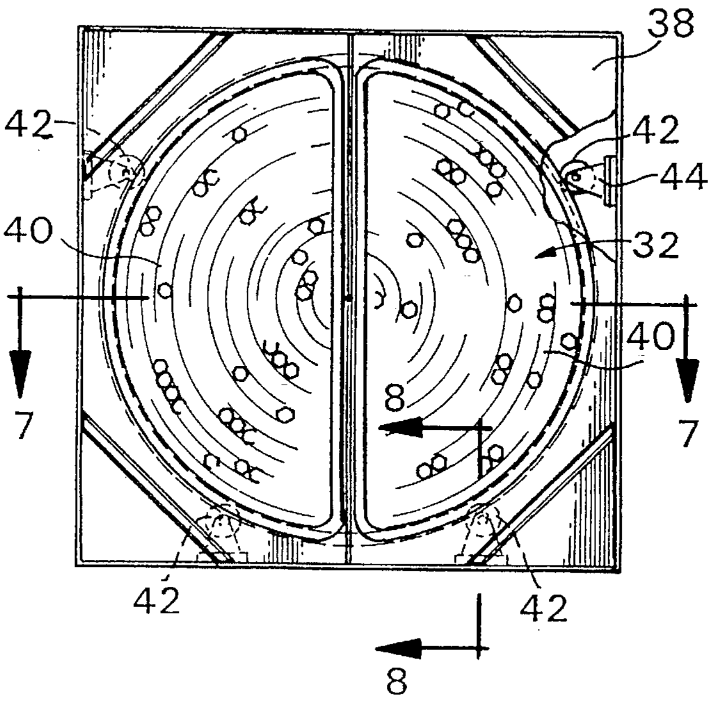
FIG. 3 is an enlarged front elevational view of the moisture transfer wheel rotatably supported within a housing.

Turning now to the construction of the moisture transfer wheel assembly 11, it comprises a moisture transfer wheel 32 and a housing 38, as illustrated in FIG. 3. The moisture transfer wheel 32 comprises a core 10 and a rim 34. The core 10 is comprised of a plurality of adjoining parallel channels 14, as illustrated in FIG. 2. According to a preferred embodiment of the core 10, each of the channels 14 is generally in the form of a hexagon in cross section and includes an internal surface area 16. It is also preferred that the channels 14 be formed from a plurality of stacked layers of material 12. The layers of material 12 of the channels 14 have a minimum thickness to inhibit the effect of the wall thickness increasing the pressure drop through the core 10 and yet provide the core 10 with sufficient structural integrity to be self supporting. In the first preferred embodiment, it is preferred that the layers of material have a thickness of about 0.0015 inch. It is understood by those skilled in the art that the exact thickness of the walls formed by the layers of material 12 could vary, depending upon the particular application of the core 10 and existing manufacturing techniques, without departing from the spirit and scope of the invention. For instance, the thickness of the walls formed by the layers of material 12 could be in the range of about 0.001 to 0.006 inch.

Each of the channels 14 includes a centrally disposed longitudinal axis 18. The channels 14 are preferably sized such that a distance between and along longitudinal axes of adjacent channels is generally uniform (i.e., the adjacent channels 14 are equidistantly spaced from each other and extend generally parallel with respect to each other). In the first preferred embodiment, it is preferred that the distance between the longitudinal axes 18 be in the range of about 0.050 to 0.125 inch. Thus, the channels 14 of the present invention, due to their hexagonal cross-sectional configuration, are closely adjoined to increase the available transfer surface per unit of volume.

In the present embodiment, it is preferred that the layers of material 12 be comprised of a non-metallic, high-strength, temperature-resistant, low thermal conductivity material, such as Nomex® aramid in paper form. The process of assembling the layers of material 12 in the form of the channels 14 is well understood by those skilled in the art. An example of a commercially available product which meets the criteria of the present invention is Aeroweb® HMX-20 without the resilient resin coating, manufactured by Ciba Composites of Anaheim, Calif., a division of Ciba Geigy Corporation of Ardsley, N.Y. However, it is understood by those skilled in the art that the layers of material 12 and the manner in which they are formed are not pertinent to the present invention, and that other materials, such as kraft paper, nylon fiber paper, mineral fiber paper and the like could be used to construct the layers of material 12 and that other methods could be used to form the hexagonal channels 14, such as extrusion, machining or molding, without departing from the spirit and scope of the invention.

In the first preferred embodiment, the internal surface area 16 is coated with a desiccant material 20 which interacts with the fluid media flowing through the channels 14 to achieve water absorption from the air. In the first preferred embodiment, it is preferred that the core 10 be used in connection with both the moisture transfer wheel assembly 11 and the heat exchanger wheel assembly 13 and that the desiccant 20 be an exchange or sorbent material which exchanges or sorbs one of heat and mass with the fluid media flowing through the channels 14. That is, it is preferred that the exchange or sorbent material be capable of removing mass or transferring heat from the fluid media flowing through the channels 14 and be capable of transferring mass or heat to the fluid media flowing through the channels 14. As used herein, the terms sorb and sorptive mean adsorption and/or absorption.

In the first preferred embodiment, it is preferred that the exchange or sorbent material be a desiccant material, such as a crystalline titanium silicate molecular sieve zeolite compound manufactured by Engelhard Corporation of Edison, N.J. under the trade name ETS and disclosed in U.S. Pat. No. 4,853,202, which is hereby incorporated by reference.

The use of channels having a cross section which is generally in the form of a hexagon is advantageous over other geometries, such as sinusoidal, square, and triangular. The following is a brief explanation of why a hexagon is better than other geometries. For a more detailed explanation, see U.S. patent application Ser. No. 08/246,548, filed May 20, 1994, which is hereby incorporated by reference in its entirety. First, the theoretical available transfer surface area (i.e., based upon standard measurements and calculations of the geometries prior to coating the interactive material) of a hexagon is greater than the transfer surface area of a sinusoidal, triangle or square for a given volume.

Second, the practical available transfer surface area (i.e., based upon standard measurements and calculations of the geometries after coating of the interactive material) of a hexagon is relatively greater, as compared to theoretical calculations, than the transfer surface area of a sinusoidal, triangle or square for a given volume because there are less surface area losses due to corner buildup. It is generally known that sorbent mass transfer is analogous to heat transfer. This relationship is defined in U.S. Pat. No. 5,148,374, which is hereby incorporated by reference, as the number of transfer units which corresponds to the effectiveness of the heat transfer. The greater the number of transfer units, the more effective the heat transfer. The number of transfer units is dependent on, among other things, the available transfer surface area. By minimizing corner build up the core 10 of the present invention achieves a number of transfer units which is equal to or greater than the number of transfer units the prior art cores achieve.

Third, the pressure drop through the core 10 of the present invention is significantly less than the core constructed of the geometries mentioned above because there is virtually no buildup in the corners of the generally hexagon shaped channels 14. Hence, the power necessary to force the fluid media through the core 10 is significantly less than that needed to force the fluid media through the prior art cores. For instance, in the case of desiccant air-conditioning systems, the reduction in power requirements allows the desiccant systems to operate at the same cost as conventional CFC air-conditioning systems for the same output of BTU's, without the inherent risk to the environment presented by CFC air-conditioning systems.

Fourth, the hexagonal core 10 provides much better bonding between channels or cells compared to the wound corrugated process described in the aforementioned patent application. Thus, the possibility for leakage of either fluid from one stream to the other at the sealing points is greatly reduced.

While in the present invention it is preferred that the channels 14 be configured to be generally in the form of a hexagon in cross section, it is understood by those skilled in the art that the cross section of the channels could be other straight-sided shapes with equal angles and equal side lengths, such that the cross section approaches a circle, and which permit the channels to be closely adjoined to maximize the greatest transfer surface area per unit volume without departing from the spirit and scope of the invention. It is also understood by those skilled in the art that other geometries could be used, such as, triangle, square, sinusoidal, so long as the operating parameters described below are attained, without departing from the scope and spirit of the invention.

The preferred method of making the core 10 comprises forming the plurality of adjoining channels 14 such that the channels 14 are generally in the form of a hexagon in cross section. As is described above, each of the channels 14 has a centrally disposed longitudinal axis 18. The internal surface area 16 of the channels 14 is then coated with a suspension of the zeolite in water, where the suspension preferably additionally contains silicate. After coating, the substrate/coating is dried to remove the water and provide zeolite adhered to the substrate. The coating of the internal surface area 16 of the channels 14 with the zeolite 20 is accomplished by forced-flow passing of the zeolite 20, as suspended in water with silicate, through the channels 14 at a laminar flow rate. The coating of surfaces using forced-flow passing is well understood by those of ordinary skill in the art and, therefore, further description thereof is omitted for purposes of convenience only. However, it is also understood by those skilled in the art that the suspension of zeolite 20 could be applied to the internal surface area 16 of the channels 14 in other manners. For instance, the zeolite 20 could be applied, in a suspension form, to the internal surface area 16 by deposition, wherein the suspension is passed through the core 10 using a non-flooding technique. Alternatively, the zeolite 20 could be applied to the layers of material 12 prior to assembling the layers of material 12 into the generally hexagonal channels 14. Or the zeolite 20 could be incorporated in the material which makes up the layers of material 12. Although it is preferred for reasons of safety and economy to use water as the suspension medium, organic solvents or mixtures of organic solvent(s) with water may also be employed.

Figure 4:
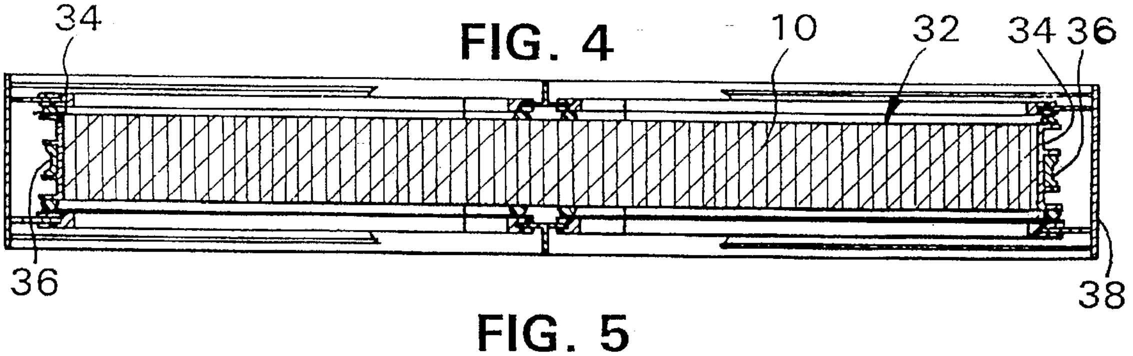
FIG. 4 is a greatly enlarged cross-sectional view of the moisture transfer wheel shown in FIG. 3 taken along lines 4—4 of FIG. 3.
Figure 5:
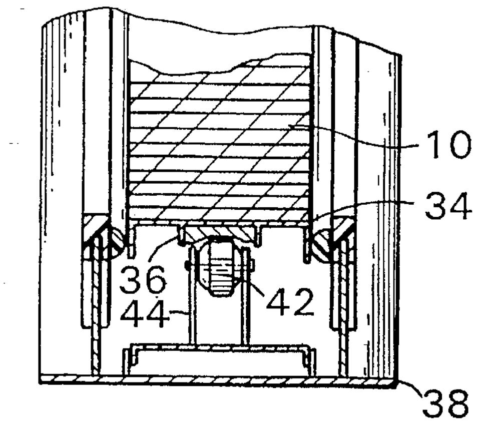
FIG. 5 is a greatly enlarged cross-sectional view of the moisture transfer wheel and housing shown in FIG. 3 taken along lines 5—5 of FIG. 3.

Referring now to FIGS. 3 through 5, there is shown the moisture transfer wheel assembly 11 having the moisture transfer wheel 32 having the core 10 disposed therein. The layers of material 12 which form the channels 14 of the core 10 provide the core 10 with sufficient structural integrity to avoid the requirement of a hub assembly and spokes, and thus in a preferred embodiment, as shown in FIG. 3, there is no hub assembly or spokes.

The rim 34 has a radially outwardly extending track 36 on its external surface. The track 36 allows the wheel 32 to be supported at its periphery, and then rotatably mounted within the housing 38, as shown in FIG. 3. The housing 38 is generally in the form of a parallelepiped and includes a pair of semi-circular openings 40 on each side to allow the wheel 32 to be placed in a desiccant air-conditioning system of the type described in U.S. Pat. No. 4,594,860. A plurality of support wheels 42 are disposed within the housing 38 and are in rolling engagement with the track 36. The support wheels 42 are positioned to rotatably support the wheel 32 in the housing 38 such that the core 10 of the wheel 32 is in alignment or registry with the semicircular openings 40. As shown in FIG. 5, the support wheels 42 are supported within the housing 38 by a generally T-shaped support member 44 which permits the support wheel 42 to rotate with respect to the support member 44 in a manner well understood by those of ordinary skill in the art. The particular manner in which the support wheels 42 are supported within the housing 38 is not pertinent to the present invention. A drive mechanism (not shown) is disposed within the housing 38 and drivingly engages the exterior of the rim 34 to rotate the wheel 32 with respect to the housing 38.

The components of the housing 38 are preferably constructed of a high-strength, lightweight material, such as aluminum. However, it is understood by those skilled in the art that the housing 38 could be constructed of other materials, such as a polymeric material or stainless steel, without departing from the spirit and scope of the invention.

The details of the mounting and driving of the wheel 32 within the housing 38 are not pertinent to the present invention. It is recognized by those of ordinary skill in the art from this disclosure that the wheel 32 can be mounted in any manner without departing from the spirit and scope of the invention. Accordingly, further description thereof is omitted for purposes of convenience only, and is not limiting.

It should be understood that while the assembly of parts shown in FIG. 1, and as described above, are a preferred structure for the desiccant air conditioner system of the present invention, the destruction of airborne microorganisms according to the invention can be achieved merely by the passage of air having a concentration of microorganisms through a core 10 comprising zeolite, as induced by, for example, either a supply blower or an exhaust blower. Indeed, for purposes of destroying airborne microorganisms according to the invention, it is not even necessary that the zeolite be regenerated, although after some time of exposure to air, the zeolite will degenerate and will no longer be effective according to the claimed method. If the zeolite is to be regenerated, it need not be regenerated according to the mechanism shown in FIG. 1, but instead the zeolite can be placed in an evacuated chamber and exposed to high temperatures therein. Standard means for regeneration of zeolites are well known in the art, and all of such means may be employed to regenerate the zeolites according to the instant invention.

It should also be understood that the heating elements 19 or 21, if present, may be powered by means other than solar energy. For example, the heating elements 19 or 20 may be powered by electricity or by internal coils of hot fluid, e.g., water or oil.

It is preferred to have the zeolites present as part of a moisture transfer wheel assembly 11, with a supply blower 23 and an exhaust blower 25 forcing air past the zeolites, as microorganism destruction and zeolite regeneration occur concurrently. The other elements of FIG. 1 are only present to further condition the air as to temperature and humidity, and may be omitted according to the invention if no or other types of conditioning is desired.

In the operation of the desiccant air conditioning system of the invention so as to achieve substantial destruction of airborne microorganisms, it is desired to have a high nominal air flow velocity through the core 10. Preferably, the nominal air flow velocity is about 200 to about 800 feet per minute (fpm), and more preferably about 400 to about 500 fpm. In a preferred embodiment, the core 10 has a zeolite density of about 0.5 to about 20 $lbs/ft^3$, and more preferably has a zeolite density of about 3 to about 8 $lbs/ft^3$. The core 10 preferably has a thickness to provide an airpath of about 2 to about 24 inches, and more preferably has a thickness of about 5 to about 10 inches. While the airpath can be made longer, only very slight additional destruction of microorganisms is observed. In a preferred embodiment, wherein the degeneration and regeneration of the zeolite occurs simultaneously as shown in FIG. 1, the core 10 rotates around its axis at a rate of about 5 to about 70 revolutions per hour (rph), and more preferably rotates at about 10 to about 40 rph.

According to a preferred embodiment, the air in the inlet path of the air conditioning system of FIG. 1 has a temperature within the range of about 0° F. to about 120° F., and a vapor pressure within the range of about 1 torr to about 25 torr prior to entering the moisture transfer wheel. According to another preferred embodiment, the air in the inlet path of the air conditioning system of FIG. 1 has a temperature of about 90° F. to about 190° F., and a vapor pressure of about 0.5 torr to about 5 torr after exiting the moisture transfer wheel.

In a preferred embodiment, the zeolite according to the invention is a large-pored crystalline titanium molecular sieve zeolite, as claimed in U.S. Pat. No. 4,853,202, (the '202 patent) the entire disclosure of which is herein incorporated by reference. This particular zeolite is preferred because, for example, it can be regenerated at a relatively low temperature when incorporated into the apparatus of FIG. 1. The zeolites of the '202 patent can be regenerated at temperatures in the range of about 170° F. to about 220° F., preferably at about 190° F. to about 200° F., and still provide sufficient drying effect to inlet air such that inlet air is dried to a vapor pressure of less than 5 torr, and typically less than 3 torr.

The preferred zeolite of the invention has the properties provided in Table 1.

TABLE 1

| XRD POWDER PATTERN OF ETS-10 (0–40° 2 theta) | |
|---|---|
| SIGNIFICANT d-SPACING (ANGS.) | $I/I_o$ |
| 14.7 = .35 | W–M |
| 7.20 = .15 | W–M |
| 4.41 = .10 | W–M |
| 3.60 = .05 | VS |
| 3.28 = .05 | W–M |

where VS = 60–100; S = 40–60; M = 20–40, and W = 5–20.

While zeolites other than those claimed in the '202 patent may be employed in the inventive method, they are not as effective at achieving the destruction of airborne microorganisms when a regeneration temperature of less than about 190° F. is used in operating the apparatus of FIG. 1.

The method according to the invention is effective at the destruction of a wide range of microorganisms, including bacteria, virus and fungi. *Candida albiens* is a representative fungus subject to destruction by the present invention. T-4 coliphage is a representative virus subject to destruction by the present invention. *Bacillus stearothermophilus, clostridiumbotulinum, clostridium perfringens, clostridium tetani, corynebacterium diphtheriae, diplococcus pneumoniae, escherichia coli, lactobacillus acidophilus, legionella pneumophilia, leptospira, mycobacterium fortuitum, mycobacterium tuberculosis, neisseria gonorrhoea, nitrosococcus, pseudomonas aeruginosa, rickettsia typhi, salmonella, shigella dysenteriae, spirocheta, staphylococcus aureus, staphylococcus epidermidis, stigmatella aurantiaca, streptococcus lactis, treponema pallidum* and *vibrio cholerae*, are representative bacteria subject to destruction by the present method.

While not intending to be bound by their theory, the inventors offer the following as an explanation for the success of the inventive method. As air is passed through a zeolite bed, water is drawn from the air and into the pores of the zeolite. This rapid exit of water from the air causes a correspondingly rapid drop in the vapor pressure of the air, and a rapid and sharp rise in the temperature of the air. Based on air flow rates, humidity changes etc., one can readily calculate that in less than one second, the air drops in vapor pressure to less than 5 torr, often less than 3 torr, and increases in temperature to at least 80° F., often in excess of 100° F. These conditions themselves, brought about by the rapid drying of the air, may be lethal to the microorganisms. However, the inventors believe that it is the speed at which the ambient conditions change which is lethal to the microorganisms: the microorganisms are unable to compensate for the sudden differential between internal and ambient pressures, and thus are destroyed. What remain after microorganism destruction are so-called ghost cells, which are essentially the ruptured cell wall without internal cytoplasm water, where water normally constitutes about 70% of the mass of the cytoplasm.

The invention will now be illustrated by the following non-limiting examples, which demonstrate the advantageous properties of the present invention,

EXAMPLES

Example 1

A desiccant air conditioning unit was installed in a nursing home to determine the antiseptic effect of the air conditioning process on airborne microorganisms. The efficacy of the unit was tested with the Anderson Six-Stage Variable Sampler (Model NG). The air was tested for bacterial and fungal load; only microbial counts were performed on the samples collected.

The guidelines used for analysis of the samples were taken from the Bioaerosols Committee of the ACGIH. Standard plastic petri plates were used, with glass plates being used periodically to provide controls. Samples for fungal counts were taken on Special Yeast and Mold agar. Bacterial samples were taken on TSA agar. Each plate contained 27 mL of medium to maintain the proper distance between the medium and the sieve plates for impaction calculations. All plates were prepared under sterile conditions.

The Anderson sampler was run at 1 ACFM for 10 minutes to sample 0.238 cubic meters of air. Between samples, the sieve plates within the sampler were sterilized using ethanol. Samples were taken at the unit's inlet and outlet.

The Special Yeast & Mold Agar plates (for fungal counts) were incubated 4–7 days under fluorescent light at room temperature prior to counting. TSA agar plates (for bacterial counts) were incubated for 48 hours at 37° C. prior to counting. If there were less than 300 colonies per plate, the counts were done visually. The bacterial counts were recorded directly as CFU (colony forming units); fungal counts were converted using the positive hole method (Andersen Manual). The number of CFUs counted on a plate was normalized to the volume of air sampled (i.e., 0.238 cubic meters), and the results reported in CFU/cubic meters. Samples were taken on Wednesdays, between 10/6/93 and terminating 12/1/93. Data from three representative samples are provided in Table 2.

TABLE 2

| Desert Cool Micro-Organism Removal Chart | | | | | | | | | | |
|---|---|---|---|---|---|---|---|---|---|---|
| Inlet Conditions | | Bacteria | Fungal | Desiccant Wheel Outlet Conditions | | | Unit Outlet Conditions | | Bacteria | Fungal |
| Temp. °F. | Vapor Pressure, Torr | Organism Count, CFU/m³ | Organism Count, CFU/m³ | Temp. °F. | Vapor Pressure, Torr | Desiccant Regeneration Temp. °F. | Temp. °F. | Vapor Pressure, Torr | Organism Count, CFU/m³ | Organism Count, CFU/m³ |
| 75.00 | 4.92 | 148.00 | 74.00 | 101.00 | 2.07 | 175.00 | 97.00 | 2.20 | 7.00 | 25.00 |
| 76.00 | 7.97 | 110.00 | 216.00 | 105.40 | 1.65 | 180.00 | 101.00 | 1.95 | 35.00 | 46.00 |
| 73.00 | 8.81 | 148.00 | 304.00 | 104.00 | 3.83 | 180.00 | 99.00 | 4.07 | 57.00 | 81.00 |

Example 2

Using the apparatus shown in FIG. 1, two zeolites were compared for their ability to achieve temperature increases, humidity decreases and vapor pressure decreases when the zeolites were present in a moisture transfer wheel and acting upon inlet air. The two zeolites were molecular sieve 4A, available from, for example, Aldrich Chemical Company, St. Louis, Miss., and denoted as "Molecular Sieve" in Table 3, and a large-pored crystalline titanium molecular sieve zeolite as claimed in U.S. Pat. No. 4,853,202, denoted as "Engelhard ETS" in Table 3, and obtained from Engelhard Corporation, Edison, N.J. The ability of these zeolites to provide air having desirably high outlet temperatures, desirably low humidity values, and desirably low vapor pressures was evaluated for three different desiccant regeneration temperatures. The regeneration temperature is the temperature of the outlet air stream immediately before entering the moisture transfer wheel.

The data in Table 3 demonstrate that the Engelhard ETS desiccant is able to provide air having high temperature, lower humidity and lower vapor pressure than can be achieved by Molecular Sieve when operating under the same reaction conditions. The data in Table 3 also demonstrate that the Engelhard ETS desiccant, when present in the moisture transfer wheel of the apparatus of FIG. 1, can provide conditioned air having a vapor pressure of less than three torr when the desiccant is regenerated with air having a temperature of not more than 190° F.

TABLE 3

Desiccant Performance Comparison
(Comparison of minimum achievable outlet humidity
180° F., 190° F. & 200° F. regeneration temperature)

| | | Inlet Conditions | | | Outlet Conditions | | |
|---|---|---|---|---|---|---|---|
| Regeneration Temp, F. | Material Type | Temp. F. | Humidity GR/lb | Vapor Pressure Torr | Temp, F. | Humidity GR/lb | Vapor Pressure Torr |
| 180.00 | Engelhard ETS | 80.00 | 78.00 | 13.22 | 138.00 | 17.20 | 2.92 |
| 180.00 | Molecular Sieve | 80.00 | 78.00 | 13.22 | 150.00 | 33.70 | 5.71 |
| 190.00 | Engelhard ETS | 80.00 | 78.00 | 13.22 | 141.00 | 12.40 | 2.10 |
| 190.00 | Molecular Sieve | 80.00 | 78.00 | 13.22 | 151.00 | 32.40 | 5.49 |
| 200.00 | Engelhard ETS | 80.00 | 78.00 | 13.22 | 145.00 | 6.00 | 1.02 |
| 200.00 | Molecular Sieve | 80.00 | 78.00 | 13.22 | 150.00 | 30.20 | 5.12 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for substantially reducing a concentration of microorganisms in air comprising passing air having the concentration of microorganisms through a desiccant air conditioning system having an inlet path, an outlet path and a moisture transfer wheel comprising zeolite, the moisture transfer wheel being positioned in the inlet and outlet paths and being movable such that the desiccant zones move between the inlet and outlet paths to degenerate and regenerate the zeolite, wherein the zeolite is regenerated at a temperature of not greater than about 190° F., and wherein the zeolite is a crystalline titaniumsilicate molecular sieve zeolite having a pore size of approximately 8 Angstrom units and a composition in terms of mole ratios of oxides as follows:

$$1.0\pm0.25\ M_{2/n}O:\ TiO_2:\ y\ SiO_2:\ z\ H_2O$$

wherein M is a least one cation having a valence of n, y is from 2.5 to 25, and z is from 0 to 100, the zeolite being characterized by an X-ray powder diffraction pattern having the lines and relative intensities as set forth in the following Table 1:

TABLE 1

| XRD POWDER PATTERN OF ETS-10 (0–40° 2 theta) | |
|---|---|
| SIGNIFICANT d-SPACING (ANGS.) | $I/I_o$ |
| 14.7 = .35 | W–M |
| 7.20 = .15 | W–M |
| 4.41 = .10 | W–M |
| 3.60 = .05 | VS |
| 3.28 = .05 | W–M |

where VS = 60–100; S = 40–60; M = 20–40, and W = 5–20.

2. A method according to claim 1 wherein the air in the inlet path has a temperature within the range of about 0° F. to about 120° F., and a vapor pressure within the range of about 1 torr to about 25 torr prior to entering the moisture transfer wheel.

3. A method according to claim 1 wherein the air in the inlet path has a temperature of about 90° F. to about 190° F., and a vapor pressure of about 0.5 torr to about 5 torr after exiting the moisture transfer wheel.

4. A method according to claim 3 wherein the vapor pressure of the air after exiting the moisture transfer wheel is not greater than 3 torr.

5. A method according to claim 1 wherein the desiccant air conditioning system is operated so as to reduce the concentration of microorganisms in the air by at least 50%.

6. A method for substantially reducing a concentration of microorganisms in air comprising passing air having the concentration of microorganisms through an open-cycle air conditioning system comprising a rotatable heat exchanger wheel, a rotatable desiccant carrying moisture transfer wheel, a heater disposed between the heat exchanger wheel and moisture transfer wheel, an evaporator positioned on a side of the heat exchanger wheel opposite from the heater, and means for passing air through the heat exchanger wheel and the moisture transfer wheel in generally separate inlet and outlet paths, wherein the air in the outlet path is at a temperature of not greater than about 190° F. prior to passing into the rotatable desiccant carrying moisture transfer wheel, and wherein the desiccant is a crystalline titaniumsilicate molecular sieve zeolite having a pore size of approximately 8 Angstrom units and a composition in terms of mole ratios of oxides as follows:

$1.0\pm0.25\ M_{2/n}O:\ TiO_2:\ y\ SiO_2:\ z\ H_2O$ wherein M is a least one cation having a valence of n, y is from 2.5 to 25, and z is from 0 to 100, the zeolite being characterized by an X-ray powder diffraction pattern having the lines and relative intensities as set forth in Table 1 below:

TABLE 1

| XRD POWDER PATTERN OF ETS-10 (0–40° 2 theta) | |
|---|---|
| SIGNIFICANT d-SPACING (ANGS.) | $I/I_o$ |
| 14.7 = .35 | W–M |
| 7.20 = .15 | W–M |
| 4.41 = .10 | W–M |
| 3.60 = .05 | VS |
| 3.28 = .05 | W–M |

where VS = 60–100; S = 40–60; M= 20–40; and W = 5–20.

7. A method according to claim 6 wherein the air in the inlet path has a temperature within the range of about 0° F. to about 120° F., and a vapor pressure of about 1 torr to about 25 torr prior to entering the moisture transfer wheel.

8. A method according to claim 6 wherein the air in the inlet path has a temperature of about 90° F. to about 190° F., and a vapor pressure of about 0.5 torr to about 5 torr after exiting the moisture transfer wheel.

9. A method according to claim 8 wherein the vapor pressure of the air after exiting the moisture transfer wheel is not greater than 3 torr.

10. A method according to claim 6 wherein the desiccant air conditioning system is operated to reduce the concentration of microorganisms in the air by at least 50%.

11. A method for substantially reducing a concentration of microorganisms in air comprising passing the air having the concentration of microorganisms through an open-cycle air conditioning system comprising a rotatable heat exchanger wheel, a rotatable zeolite carrying moisture transfer wheel, a heater disposed between the heat exchanger wheel and moisture transfer wheel, an evaporator positioned on a side of the heat exchanger wheel opposite from the heater, and means for passing air through the heat exchanger wheel and the moisture transfer wheel in an inlet path and an outlet path, wherein the air in the outlet path is at a temperature of not greater than about 190° F. prior to passing into the rotatable zeolite carrying moisture transfer wheel, and wherein the zeolite is a crystalline titaniumsilicate molecular sieve zeolite having a pore size of approximately 8 Angstrom units and a composition in terms of mole ratios of oxides as follows:

$1.0\pm0.25\ M_{2/n}O:\ TiO_2:\ y\ SiO_2:\ z\ H_2O$ wherein M is a least one cation having a valence of n, y is from 2.5 to 25, and z is from 0 to 100, the zeolite being characterized by an X-ray powder diffraction pattern having the lines and relative intensities as set forth in Table 1 below:

TABLE 1

| XRD POWDER PATTERN OF ETS-10 (0–40° 2 theta) | |
|---|---|
| SIGNIFICANT d-SPACING (ANGS.) | $I/I_o$ |
| 14.7 = .35 | W–M |
| 7.20 = .15 | W–M |
| 4.41 = .10 | W–M |
| 3.60 = .05 | VS |
| 3.28 = .05 | W–M |

where VS = 60–100; S = 40–60; M = 20–40, and W = 5–20.

12. A method according to claim 11 wherein the air in the inlet path has a temperature within the range of about 0° F. to about 120° F., and a vapor pressure of about 1 torr to about 25 torr prior to entering the moisture transfer wheel.

13. A method according to claim 11 wherein the air in the inlet path has a temperature of about 90° F. to about 190° F., and a vapor pressure of about 0.5 torr to about 5 torr after exiting the moisture transfer wheel.

14. A method according to claim 13 wherein the vapor pressure of the air after exiting the moisture transfer wheel is not greater than 3 torr.

15. A method according to claim 11 wherein the desiccant air conditioning system is operated to reduce the concentration of microorganisms in the air by at least 50%.

16. A method according to claim 11 wherein the inlet and outlet paths are generally separate.

17. A method of controlling an open-cycle desiccant air conditioning system having a rotatable heat exchanger wheel, a rotatable desiccant carrying moisture transfer wheel, a heater disposed between the heat exchanger wheel and moisture transfer wheel, an evaporator positioned on a side of the heat exchanger wheel opposite from the heater, and means for passing air through the heat exchanger wheel and the moisture transfer wheel in an inlet path and an outlet path, to substantially reduce a concentration of microorganisms in air forced through the air conditioning system, comprising the steps of:

a. inleting air to the system where the air has a temperature within the range of about 0° F. to about 120° F. and a vapor pressure of about 1 torr to about 25 torr;

b. exiting inlet air from the moisture transfer wheel where the air has a vapor pressure of no more than 5 torr; and c. drawing outlet air having a temperature not exceeding about 190° F. through the moisture transfer wheel; and wherein the desiccant is a crystalline titaniumsilicate molecular sieve zeolite having a pore size of approximately 8 Angstrom units and a composition in terms of mole ratios of oxides as follows:

$1.0\pm0.25\ M_{2/n}O: TiO_2: y\ SiO_2: z\ H_2O$ wherein M is a least one cation having a valence of n, y is from 2.5 to 25, and z is from 0 to 100, the zeolite being characterized by an X-ray powder diffraction pattern having the lines and relative intensities as set forth in Table 1 below:

TABLE 1

| XRD POWDER PATTERN OF ETS-10 (0–40° 2 theta) SIGNIFICANT d-SPACING (ANGS.) | $I/I_o$ |
|---|---|
| 14.7 = .35 | W–M |
| 7.20 = .15 | W–M |
| 4.41 = .10 | W–M |
| 3.60 = .05 | VS |
| 3.28 = .05 | W–M |

where VS = 60–100; S = 40–60; M = 20–40, and W = 5–20.

where VS=60–100; S=40–60; m=20–40; and W=5–20.

18. A method according to claim 17 wherein the inlet air exiting from the moisture transfer wheel has a vapor pressure of less than about 3 torr.

* * * * *